(12) United States Patent
Tischner et al.

(10) Patent No.: US 6,727,095 B1
(45) Date of Patent: Apr. 27, 2004

(54) NUCLEOTIDE SEQUENCES ENCODING SUGARBEET GLUTAMINE SYNTHETASE AND METHODS FOR REDUCING GLUTAMINE METABOLISM IN SUGARBEET

(75) Inventors: Rudolf Tischner, Göttingen (DE); Guido Hoffmann, Göttingen (DE)

(73) Assignee: Sudzucker Aktiengesellschaft (DE)

( * ) Notice: Subject to any disclaimer, the term of this patent is extended or adjusted under 35 U.S.C. 154(b) by 0 days.

(21) Appl. No.: 09/786,534

(22) PCT Filed: Sep. 4, 1999

(86) PCT No.: PCT/EP99/06522

§ 371 (c)(1),
(2), (4) Date: Jun. 26, 2001

(87) PCT Pub. No.: WO00/14247

PCT Pub. Date: Mar. 16, 2000

(30) Foreign Application Priority Data

Sep. 8, 1998 (DE) .......................................... 198 40 964

(51) Int. Cl.[7] .................... C12N 15/29; C12N 15/82; C12N 15/90; A01H 5/00; A01H 5/10
(52) U.S. Cl. .................... 435/468; 435/320.1; 435/471; 536/23.6; 800/278; 800/286; 800/298
(58) Field of Search .................... 435/320.1, 410, 435/419, 471, 468, 483; 536/23.6; 800/278, 285, 286, 287, 295, 298

(56) References Cited

FOREIGN PATENT DOCUMENTS

| WO | 91/13159 | 9/1991 | ............ C12N/15/82 |
|---|---|---|---|
| WO | 95/09911 | 4/1995 | ............ C12N/15/00 |
| WO | 97/38115 | 10/1997 | ............ C12N/15/82 |

OTHER PUBLICATIONS

Kochert, et al, 1993, "Influence of Wetting Agents on the Foliar Uptake and Herbidical Activity of Glufosinate*", Pestic. Sci. vol. 37, pp. 155–158.*

S.J. Temple, et al., "Modulation of Glutamine Synthetase Gene Expression in Tobacco by the Production of an Alfalfa Glutamine Synthetase Gene in Sense and Tisense Orientation: Molecular and Biochemical Analysis", *Mol Gen Genet*, Jan. 1993, vol. 236, Nos. 2–3, pp. 315–325.

S.J. Temple, et al., "Down–Regulation of Specific Members of the Glutamine Synthetase Gene Family in Alfalfa by Antisense RNA Technology", *Plant Mol Biol*, Jun. 1998, vol. 37, No. 3, pp. 535–547.

G. Maock, et al., "—Glutamine—Synthetase Oligomers and Isoforms in Sugar Beet Beta–Vulgaris L.", *Planta (Heidelberg)*, 1990, vol. 181, No. 1, pp. 10–17.

R. Vincent, et al., "Overexpression of A Soybean Gene Encoding Cytosolic Glutamine Synthetase Shoots of Transgenic Lotus Corniculatus L. Plants Triggers Changes in Monium Assimilation and Plant Development", *Planta 1997*, vol. 201, No. 4, pp. 424–433.

G. Maock, "Glutamine Synthetase Isoenzymes, Oligomers, and Subunits from Hairy Roots of—Beta—Vulgaris—Var. Lutea", *Planta (1998)*, May 1998, vol. 205, No. 1, pp. 113–120.

P. Brechlin, et al., "Changes in the Isoform Pattern and Subunit Composition of GS–1 in Sugar Beet Leaves Dependent on Leaf Age", *J. of Plant Physiology*, Oct. 1999, vol. 155, Nos. 4–5, pp. 497–502.

E. Carrayol, et al., "Ammonia Regulated Expression of A Soybean Gene Encoding Cytosolic Glutamine Synthetase is not Conserved in Two Heterologous Plant Systems", *Plant Science*, 1997, vol. 125, pp. 75–85.

J.W. Edwards, et al., "Photorespiration and Light Act in Concert to Regulate the Expression of the Nuclear Gene for Chloroplast Glutamine Synthetase", *The Plant Cell*, Feb. 1989, vol. 1, pp. 241–248.

S.J. Temple, et al., "Characterization of a Nodule–Enhanced Glutamine Synthetase From Alfalfa: Nucleotide Sequence, In–Situ Localisation, and Transcript Analysis", *EMBL Sequence Data Library*, Nov. 5, 1994, Heidelberg, Germany. EMBL Acc. No. U15591.

* cited by examiner

Primary Examiner—Ashwin Mehta
(74) Attorney, Agent, or Firm—Ostrolenk Faber Gerb & Soffen, LLP (57) ABSTRACT

The present invention relates to agents and methods for modifying the glutamine metabolism in plants, especially in sugar beet.

15 Claims, 2 Drawing Sheets

SEQUENCE LISTING

<160> NUMBER OF SEQ ID NOS: 3

<210> SEQ ID NO 1
<211> LENGTH: 1068
<212> TYPE: DNA
<213> ORGANISM: Beta vulgaris
<220> FEATURE:
<221> NAME/KEY: CDS
<222> LOCATION: (1)..(1068)

<400> SEQUENCE: 1

```
atg gct ctt ctt aac gat cta att aac ctt aat ctc tca gaa aca tct      48
Met Ala Leu Leu Asn Asp Leu Ile Asn Leu Asn Leu Ser Glu Thr Ser
 1               5                  10                  15 gac aag att att gct gag tat ata tgg atc gga gga tct ggg ttg gat      96
Asp Lys Ile Ile Ala Glu Tyr Ile Trp Ile Gly Gly Ser Gly Leu Asp
            20                  25                  30 atg aga agc aaa gca agg aca tta aca ggg cca ata agt gat cct gca     144
Met Arg Ser Lys Ala Arg Thr Leu Thr Gly Pro Ile Ser Asp Pro Ala
        35                  40                  45 aaa tta cca aaa tgg aat tac gat gga tca agt act aat caa gct cct     192
Lys Leu Pro Lys Trp Asn Tyr Asp Gly Ser Ser Thr Asn Gln Ala Pro
    50                  55                  60 ggt gaa gat agt gaa gtc att tta tac cct cag gct att ttc aag gat     240
Gly Glu Asp Ser Glu Val Ile Leu Tyr Pro Gln Ala Ile Phe Lys Asp
65                  70                  75                  80 cca ttc aga aga gga gac aat atc cta gtt atg tgt gat gca tac acc     288
Pro Phe Arg Arg Gly Asp Asn Ile Leu Val Met Cys Asp Ala Tyr Thr
                85                  90                  95 cca gct gga gaa cca att cca aca aac aag agg tac aat gct gag aaa     336
Pro Ala Gly Glu Pro Ile Pro Thr Asn Lys Arg Tyr Asn Ala Glu Lys
            100                 105                 110 atc ttc agc cac cca gac gtt gtc gct gag gag cca tgg tat gga att     384
Ile Phe Ser His Pro Asp Val Val Ala Glu Glu Pro Trp Tyr Gly Ile
        115                 120                 125 gaa caa gaa tac aca ctt ctt cag aag gat atc aac tgg cct ctt gga     432
Glu Gln Glu Tyr Thr Leu Leu Gln Lys Asp Ile Asn Trp Pro Leu Gly
    130                 135                 140 tgg cca act ggt ggc ttc cct ggt cct cag gga cca tac tat tgt ggt     480
Trp Pro Thr Gly Gly Phe Pro Gly Pro Gln Gly Pro Tyr Tyr Cys Gly
145                 150                 155                 160 gta ggg gct gat aaa tct ttc ggg cga gac att gta gat gct cac tat     528
Val Gly Ala Asp Lys Ser Phe Gly Arg Asp Ile Val Asp Ala His Tyr
                165                 170                 175 aag gct tgc atc tat gct ggt gtc aat atc agt gga att aat ggt gaa     576
Lys Ala Cys Ile Tyr Ala Gly Val Asn Ile Ser Gly Ile Asn Gly Glu
            180                 185                 190 gtc atg cca gga cag tgg gaa ttc caa gtt ggt cct act gtt gga att     624
Val Met Pro Gly Gln Trp Glu Phe Gln Val Gly Pro Thr Val Gly Ile
        195                 200                 205 tca tct ggt gat caa gtc tgg gtt gct aga tac att ctt gag aga att     672
```

-continued

```
Ser Ser Gly Asp Gln Val Trp Val Ala Arg Tyr Ile Leu Glu Arg Ile
        210                 215                 220 gct gag att gcc gga gtt gtt gtg tct ttt gac ccc aaa cca gtg aag     720
Ala Glu Ile Ala Gly Val Val Val Ser Phe Asp Pro Lys Pro Val Lys
225                 230                 235                 240 ggt gat tgg aat ggt gct ggt gct cac acc aac tac agc act aag tcg     768
Gly Asp Trp Asn Gly Ala Gly Ala His Thr Asn Tyr Ser Thr Lys Ser
                245                 250                 255 atg agg gaa gat ggt ggg atc aat gtt ata aag gct gcc atc gag aag     816
Met Arg Glu Asp Gly Gly Ile Asn Val Ile Lys Ala Ala Ile Glu Lys
            260                 265                 270 ttg agt ctc cgt cac aag gag cac att gct gcc tac ggg gag ggc aac     864
Leu Ser Leu Arg His Lys Glu His Ile Ala Ala Tyr Gly Glu Gly Asn
        275                 280                 285 gag agg agg ctc act ggt cgt cat gag aca gcc gat atc acc act ttc     912
Glu Arg Arg Leu Thr Gly Arg His Glu Thr Ala Asp Ile Thr Thr Phe
    290                 295                 300 tcc tgg ggt gtt gca aat agg ggt gcc tct gtt cgt gtt ggc cgt gac     960
Ser Trp Gly Val Ala Asn Arg Gly Ala Ser Val Arg Val Gly Arg Asp
305                 310                 315                 320 aca gag aaa gat ggc aaa ggt tac ttt gaa gac aga agg cca gca tca    1008
Thr Glu Lys Asp Gly Lys Gly Tyr Phe Glu Asp Arg Arg Pro Ala Ser
                325                 330                 335 aac atg gat cca tat gtg gtt acc tcc atg att gct gaa aca act atc    1056
Asn Met Asp Pro Tyr Val Val Thr Ser Met Ile Ala Glu Thr Thr Ile
            340                 345                 350 ctc gga aag cct                                                    1068
Leu Gly Lys Pro
        355
```

<210> SEQ ID NO 2
<211> LENGTH: 356
<212> TYPE: PRT
<213> ORGANISM: Beta vulgaris

<400> SEQUENCE: 2

```
Met Ala Leu Leu Asn Asp Leu Ile Asn Leu Asn Leu Ser Glu Thr Ser
 1               5                   10                  15

Asp Lys Ile Ile Ala Glu Tyr Ile Trp Ile Gly Gly Ser Gly Leu Asp
                20                  25                  30

Met Arg Ser Lys Ala Arg Thr Leu Thr Gly Pro Ile Ser Asp Pro Ala
            35                  40                  45

Lys Leu Pro Lys Trp Asn Tyr Asp Gly Ser Ser Thr Asn Gln Ala Pro
        50                  55                  60

Gly Glu Asp Ser Glu Val Ile Leu Tyr Pro Gln Ala Ile Phe Lys Asp
65                  70                  75                  80

Pro Phe Arg Arg Gly Asp Asn Ile Leu Val Met Cys Asp Ala Tyr Thr
                85                  90                  95

Pro Ala Gly Glu Pro Ile Pro Thr Asn Lys Arg Tyr Asn Ala Glu Lys
            100                 105                 110

Ile Phe Ser His Pro Asp Val Ala Glu Glu Pro Trp Tyr Gly Ile
        115                 120                 125

Glu Gln Glu Tyr Thr Leu Leu Gln Lys Asp Ile Asn Trp Pro Leu Gly
    130                 135                 140

Trp Pro Thr Gly Gly Phe Pro Gly Pro Gln Gly Pro Tyr Tyr Cys Gly
145                 150                 155                 160

Val Gly Ala Asp Lys Ser Phe Gly Arg Asp Ile Val Asp Ala His Tyr
                165                 170                 175
```

-continued

```
        Lys Ala Cys Ile Tyr Ala Gly Val Asn Ile Ser Gly Ile Asn Gly Glu
                    180                 185                 190

Val Met Pro Gly Gln Trp Glu Phe Gln Val Gly Pro Thr Val Gly Ile
                    195                 200                 205

Ser Ser Gly Asp Gln Val Trp Val Ala Arg Tyr Ile Leu Glu Arg Ile
                    210                 215                 220

Ala Glu Ile Ala Gly Val Val Ser Phe Asp Pro Lys Pro Val Lys
        225                 230                 235                 240

Gly Asp Trp Asn Gly Ala Gly Ala His Thr Asn Tyr Ser Thr Lys Ser
                    245                 250                 255

Met Arg Glu Asp Gly Gly Ile Asn Val Ile Lys Ala Ala Ile Glu Lys
                    260                 265                 270

Leu Ser Leu Arg His Lys Glu His Ile Ala Ala Tyr Gly Glu Gly Asn
                    275                 280                 285

Glu Arg Arg Leu Thr Gly Arg His Glu Thr Ala Asp Ile Thr Thr Phe
                    290                 295                 300

Ser Trp Gly Val Ala Asn Arg Gly Ala Ser Val Arg Val Gly Arg Asp
        305                 310                 315                 320

Thr Glu Lys Asp Gly Lys Gly Tyr Phe Glu Asp Arg Arg Pro Ala Ser
                    325                 330                 335

Asn Met Asp Pro Tyr Val Val Thr Ser Met Ile Ala Glu Thr Thr Ile
                    340                 345                 350

Leu Gly Lys Pro
                    355

<210> SEQ ID NO 3
<211> LENGTH: 1534
<212> TYPE: DNA
<213> ORGANISM: Beta vulgaris

<400> SEQUENCE: 3
gaattgggta ccgggccccc cctcgaggtc gacggtatcg ataagcttga tatcgaattc      60
cgttgctgtc gccgttgctg tcgccgttgc tgtcgccgtt gctgtcgccg ttgctgtcgg     120
cggccgcttt tttttttttt tttttctctc tcttcatttt cttcactttt tcttcttcat     180
aacaaaaaat catcaatcat ggctcttctt aacgatctaa ttaaccttaa tctctcagaa     240
acatctgaca agattattgc tgagtatata tggatcggag gatctgggtt ggatatgaga     300
agcaaagcaa ggacattaac agggccaata agtgatcctg caaaattacc aaaatggaat     360
tacgatggat caagtactaa tcaagctcct ggtgaagata gtgaagtcat tttataccct     420
caggctattt tcaaggatcc attcagaaga ggagacaata tcctagttat gtgtgatgca     480 tacacccag ctggagaacc aattccaaca acaagaggt acaatgctga gaaaatcttc      540
agccacccag acgttgtcgc tgaggagcca tggtatgaa ttgaacaaga atacacactt      600
cttcagaagg atatcaactg gcctcttgga tggccaactg gtggcttccc tggtcctcag     660
ggaccatact attgtggtgt aggggctgat aaatctttcg gcgagacat tgtagatgct      720 cactataagg cttgcatcta tgctggtgtc aatatcagtg gaattaatgg tgaagtcatg     780
ccaggacagt gggaattcca agttggtcct actgttggaa tttcatctgg tgatcaagtc     840
tgggttgcta gatacattct tgagagaatt gctgagattg ccggagttgt tgtgtctttt     900
gaccccaaac cagtgaaggg tgattggaat ggtgctggtg ctcacaccaa ctacagcact     960
aagtcgatga gggaagatgg tgggatcaat gttataaagg ctgccatcga gaagttgagt    1020
```

-continued

```
ctccgtcaca aggagcacat tgctgcctac ggggagggca acgagaggag gctcactggt    1080
cgtcatgaga cagccgatat caccactttc tcctggggtg ttgcaaatag gggtgcctct    1140
gttcgtgttg gccgtgacac agagaaagat ggcaaaggtt actttgaaga cagaaggcca    1200
gcatcaaaca tggatccata tgtggttacc tccatgattg ctgaaacaac tatcctcgga    1260
aagccttgaa aacattataa ttaattccgc atttcaatat atcttcatgt gaatttggat    1320
aacaattgga gttgtatttg tgattagaca actattttac attttctcca ggtttgaaat    1380
aaattatctg tacgttgttc tgaattttt tccttatctt ttgcttgata gtacaaggaa     1440
atttggcttc acatgttaat atgatggctt ctttggtaaa aaaaaaaaa aaaaaaaaa      1500 aaaaaaaagc ggccgccacc gcggtggagc tcca                                1534
```

NUCLEOTIDE SEQUENCES ENCODING SUGARBEET GLUTAMINE SYNTHETASE AND METHODS FOR REDUCING GLUTAMINE METABOLISM IN SUGARBEET

DESCRIPTION

The present invention relates to the nucleotide sequence of a glutamine synthetase from sugarbeet, to a vector comprising this nucleotide sequence, to cells which are transformed with this vector, to proteins encoded by this nucleotide sequence, to plants which have been transformed with this nucleotide sequence, and to methods for the genetic modification of plants, in particular sugarbeet.

The accumulation of glutamine as the main α-amino-N component which occurs in the storage root, that is to say the storage organ of the sugarbeet, and which is also referred to as harmful nitrogen, gives rise to considerable problems in sugar production. The compensation, generally by rendering alkaline, for the acidification of the beet juice which is caused by this component is costly, leads to faster wear on the production systems and, finally, also involves considerable environmental pollution, which can likewise be prevented only by use of costly measures. This glutamine is synthesized in the plant through amidation of glutamic acid by $NH_4^+$ being bound, with consumption of ATP, to C-4 of glutamate. This step is catalyzed by the enzyme glutamine synthetase (abbreviated to GS hereinafter). This enzyme is present both in the chloroplast and in the cytoplasm of the plant cell. In the chloroplast, the enzyme occurs as a tetramer which is encoded by one gene and consists of up to five subunits (GS-2). In the cytoplasm, according to current knowledge, the enzyme normally occurs as a heterooligomer (GS-1) encoded by more than one gene. The various GS-1 isoenzymes known are usually heterooctamers. Six different isoforms of GS-1 have been found to date. The glutamine synthetase localized in the chloroplast, that is to say GS-2, has the main function of binding the $NH_4^+$ produced during photorespiration and converting the $NH_4^+$ derived from nitrate reduction into organic compounds. The function of GS-1 is, by contrast, mainly in catabolic degradation pathways during the course of which the $NH_{4+}$ resulting from protein degradation is fixed. Such degradation pathways are particularly important during aging of the leaf, that is to say during senescence, and the resulting glutamine is exported from the leaf into storage organs.

In contrast to GS-2 in the chloroplast, relatively little is known about GS-1 in the cytoplasm. This relates in particular to its function in the cell, but also to its regulation. In contrast to GS-2, it has been assumed to date that GS-1 is encoded by more than one gene, the number thereof being variable. The genes show homologies with one another but can be unambiguously separated from one another (Brears et al., Plant J. 1 (1991), 235 to 244; Edwards et at al., Plant Cell 1 (1989), 241 to 248). In addition, the GS-1 genes, which each encode one subunit of the octameric holoenzyme, appear to be regulated differently (Petermann and Goodman MGG 230 (1991), 145 to 154). Controlled external influencing of glutamine metabolism by modification of GS-1 is made difficult thereby.

The localization of GS-1 in the plant is also still substantially unknown. It is known from Edwards et al. (loc. cit.) that one isoform is thought to be expressed exclusively in the phloem, where it possibly plays a part in intercellular transport. Sakurai et al. (Planta 200 (1996), 306 to 311) reports that in rice one isoform of GS-1 is present in the conducting bundles and evidently plays a part in the export of glutamine from leaves. It is also known that tobacco and alfalfa plants which have been transformed with a GS-1 gene from Lotus corniculatus show expression in the flowers (Carrayol et al., Plant Sci 125 (1997), 75 to 85). It is additionally known that the composition and localization of GS-1 holoenzymes in the root nodules of Lotus corniculatus may vary greatly.

No targeted reduction, carried out by methods of molecular biology, in the glutamine content in plants, especially in storage organs of plants, has been disclosed to date. The essential difficulties occurring in the targeted reduction of the glutamine synthetase activity in plants and the eventually desired reduction in the nitrogen content in storage organs of plants derive from the fact that the glutamine synthetase activity must be restricted tissue- and time-specifically in such a way that the nitrogen content in the target organ, for example the storage root of a sugarbeet, is reduced. This must not involve any impairment of the other functions and properties of the sugarbeet. On the contrary, it must be ensured that the overall physiology of the sugarbeet remains intact and there is merely a specific reduction in the nitrogen content in the storage organ of the sugarbeet. Because of the problems described concerning the localization of GS-1 and the lack of clarity in relation to the time specificity of its activity, no successful experiments have been disclosed indicating that it was possible to reduce the nitrogen content in storage organs of sugarbeet via modulation of the GS-1 activity.

The technical problem on which the present invention is based is thus to provide means and methods which make it possible in a targeted manner, that is to say tissue- and time-specifically, to reduce the nitrogen content in the storage organ of a plant, in particular of a sugarbeet, without this involving impairment of the vital, growth and reproductive functions of the sugarbeet and its commercial value.

The present invention solves this problem by providing an isolated and purified nucleotide sequence and vectors comprising this nucleotide sequence, which code for one subunit of the GS-1 of sugarbeet. The present invention solves the technical problem also by providing the isolated and purified protein encoded by this nucleotide sequence, in particular the amino acid sequence of the GS-1 subunit from sugarbeet, and by methods for the genetic modification of plants, in particular sugarbeet, where the content of glutamine synthetase in a plant, in particular in its senescent leaves, is altered, in particular reduced, by transforming cells of this plant with said vectors, and regenerating from the transformed cells intact, propagatable, stably transformed transgenic plants in whose senescent leaves the activity of GS-1 is reduced or completely suppressed.

The invention is surprising and advantageous in particular because the subunit encoded by the nucleotide sequences of the invention represents the only subunit of the oligomeric GS-1 isoform occurring in the senescent leaves of the sugarbeet. Accordingly, the invention also provides the surprising information that this isoform of GS-1 is a homooctamer. This makes it possible in a surprising manner to influence the activity of this enzyme by influencing the expression of a single gene, namely the gene encoding the GS-1 subunit, in particular to prevent or reduce the expression thereof. The invention is also surprising inasmuch as the homooligomeric isoform of GS-1 provided by the invention occurs only in the stage of senescence and accordingly displays, besides the tissue specificity in relation to the localization in the leaf which has been mentioned above, also a time specificity in relation to the occurrence during senescence. The present invention surprisingly therefore provides means and methods for influencing the qualitative and/or quantitative occurrence of a homooctameric GS-1 isoform which can be found only in senescent leaves of the sugarbeet. The nucleotide sequences of the invention can also be used for cloning homologous genes, in particular the coding regions thereof, in other tissues and even other plants and organisms. It is possible in particular on use of the present nucleotide sequence as hybridization probe in homologous or heterologous systems also to identify and isolate endogenous regulatory noncoding nucleotide sequences which are associated with this sequence and which, for example, mediate time- and tissue-specific expression.

The invention solves the present technical problem in particular by providing a nucleotide sequence for modulating the expression, in particular for suppressing the expression, of a protein having the activity of a glutamine synthetase, in particular the activity of a GS-1, which is selected from the group consisting of a) the DNA sequence of SEQ ID No. 1, 3 or a part thereof,
b) a nucleotide sequence which encodes the amino acid sequence of SEQ ID No. 2 or a part thereof,
c) a nucleotide sequence which is complementary to the nucleotide sequences of a) or b), or a part thereof, and
d) a nucleotide sequence which hybridizes with the nucleotide sequences of a) to c).

The nucleotide sequence of the invention is functionally characterized in that, in a cell transformed therewith and having an endogenous GS-1-encoding sequence, it modulates the activity of the GS-1 activity of this transformed cell, for example increases the GS-1 activity, for example by overexpression, or reduces or completely suppresses the GS-1 activity, for example through the nucleotide sequence of the invention being transformed in the form of an antisense construct which inhibits endogenous GS-1 translation.

The invention provides in a particularly preferred embodiment for the nucleotide sequence to be derived from the sugarbeet *Beta vulgaris*.

The nucleotide sequence of the invention may be a DNA sequence, for example a genomic, where appropriate. intron-interrupted DNA sequence or CDNA sequence, but it can also be an RNA sequence, for example an mRNA sequence or synthetically prepared. The present invention relates both to the sense and to the antisense nucleotide sequences. The nucleotide sequences of the invention can be so-called full-length sequences, that is to say sequences which encode a complete protein having the activity of a glutamine synthetase, in particular of the GS-1 of sugarbeet, where appropriate including the translation initiation site. However, the invention also relates to partial sequences of such nucleotide sequences, in particular those which serve to modulate the expression of the protein having the activity of a glutamine synthetase, in particular of a GS-1 from sugarbeet. Accordingly, the nucleotide sequence of the invention may also form a fusion gene in a transcription or translation unit with other nucleotide sequences. The invention relates in an advantageous refinement also to nucleotide sequences which hybridize with the DNA sequence specified in SEQ ID No. 1 or 3 or hybridize with a nucleotide sequence which encodes the amino acid sequence of SEQ ID No. 2, and nucleotide sequences which hybridize with nucleotide sequences complementary tothe two sequences mentioned.

In connection with the present invention, hybridization means a prehybridization, a hybridization and subsequent washing. The prehybridization preferably takes place in an aqueous solution composed of 6×SSPE, 0.1% SDS and 5×Denhardt's reagent, and 500 µg/ml denatured herring sperm at 60° C., particularly preferably at 65° C., for 3 hours. The hybridization preferably takes place in an aqueous solution composed of 3×SSPE, 0.1% SDS, 5×Denhardt's reagent and 500 µg/ml denatured herring sperm at 60° C., particularly preferably at 65° C., for 16 hours. The washing preferably takes place in an aqueous solution composed of 2×SSPE and 0.1% SDS at room temperature for 10 minutes, this being followed by another washing step in an aqueous solution composed of 2×SSPE and 0.1% SDS at 60° C., particularly preferably at 65° C., for 15 minutes and by a final washing step with an aqueous solution composed of 0.4×SSPE and 0.02% SDS at 60° C., particularly preferably at 65° C., for 15 minutes.

In a particularly preferred embodiment, a prehybridization is carried out in an aqueous solution composed of 6×SSPE, 0.1% SDS and 5×Denhardt's reagent, and 500 µg/ml denatured herring sperm at 65° C. for 3 hours. The hybridization takes place in an aqueous solution composed of 3×SSPE, 0.1% SDS, 5×Denhardt's reagent and 500 µg/ml denatured herring sperm at 68° C. for 16 hours. The washing takes place in an aqueous solution composed of 2×SSPE and 0.1% SDS at 68° C. for 15 minutes, this being followed by another washing step in an aqueous solution composed of 1×SSPE and 0.1% SDS at 68° C. for 15 minutes and by a final washing step with an aqueous solution composed of 0.1×SSPE and 0.1% SDS at 68° C. for 15 minutes.

The present invention also relates, of course, to modifications of the aforementioned sequences, in particular those which display, by comparision with the sequences shown in SEQ ID No. 1 or 3, nucleotide additions, deletions, inversions, substitutions or the like, including chemical derivatizations or replacement, exchange or addition of unusual nucleotides.

The invention also relates to nucleotide sequences which have a degree of homology of at least 80%, preferably 90%, to the sequences shown in SEQ ID No. 1 or 3.

The nucleotide sequences of the present invention are advantageous in particular inasmuch as they serve to modulate the expression of a protein having the activity of a glutamine synthetase, in particular the GS-1 from sugarbeet. The nucleotide sequences of the invention can be employed for altering, in particular reducing, and in a particularly preferred manner completely suppressing, the amount of glutamine synthetase formed, in particular the GS-1 from sugarbeet. In a particularly preferred manner, the invention makes it possible through modulation of the expression in a tissue- and time-specific manner for the deposition of glutamine in the storage organ of the sugarbeet to be suppressed without this inevitably entailing the need to employ tissue- and time-specific regulatory elements for the transgene, that is to say the nucleotide sequence of the invention. This is because the nucleotide sequences of the invention encode the GS-1 of sugarbeet, which occurs specifically only in senescent leaves, and accordingly shows site specificity in relation to the expression in leaves and time specificity in relation to the expression during senescence. The nucleotide sequences of the invention make it possible to inhibit this glutamine synthetase, which occurs specifically at leaf senescence, by means of a single gene construct because the GS-1 of sugarbeet is a homooctamer and accordingly the formation of all the GS-1 subunits can be switched off by means of a single gene construct. Accordingly, the invention provides in a particularly preferred manner for the use of antisense constructs which specifically suppress the formation of protein, that is to say GS-1, in the senescent leaves of sugarbeet. It is possible by use of antisense constructs to inhibit the expression of the GS-1 of sugarbeet which occurs specifically at leaf senescence, so that glutamine formation and deposition of glutamine in the storage root is prevented. The growth of the sugarbeet is advantageously not impaired in this process because GS-2 is not affected by the genetic manipulation of the plant cell.

In connection with the present invention, the activity of a protein having the activity of a glutamine synthetase means an activity by which $NH_4^+$ is bound enzymatically to C-4 of a glutamate molecule with use of ATP.

In connection with the present invention, modulation of the expression of a protein means a deliberate change, that is to say increase or reduction, achieved by genetic engineering methods, in the amount of protein in a cell compared with the amount of protein naturally present in the relevant cell at the relevant time.

The modulation of expression can take place by influencing the translation or transcription of the endogenous nucleotide sequence encoding the protein, for example by introducing an antisense construct which partially or completely reduces the amount of translatable mRNA. An increase in the amount of protein may take place, for example, by introducing a nucleotide sequence which encodes the protein and is under the control of overexpressing regulatory elements, or by introducing multiple gene copies.

Further alternative or additional modulations can be achieved by employing tissue- or time-specific, inducible or constitutively expressed regulatory elements which lead to an expression pattern which is altered by comparison with the natural expression pattern in the relevant cell and at the relevant time or at the relevant stage of development of the cell or the plant.

The present invention relates in a further embodiment to vectors comprising at least one of the nucleotide sequences of the invention. In a particularly preferred embodiment of the invention, such a vector is embodied as plasmid or viral vector.

The present invention also relates to vectors of the aforementioned type, where the at least one nucleotide sequence of the present invention is under the control of regulatory nucleotide sequences which are likewise present in the vector and which are arranged, for example, 5', 3', 5' and 3' or else within the nucleotide sequence. These regulatory nucleotide sequences may be heterologous to the nucleotide sequence of the invention, that is to say be derived from a different organism or from a different gene, or homologous, that is to say also naturally occurring together with the nucleotide sequences of the invention in a regulatory unit.

The invention accordingly also relates to vectors of the aforementioned type, where a nucleotide sequence controlling the expression of the nucleotide sequence of the invention, in particular a promoter, is located 5'-wards of the nucleotide sequence of the invention. In a particularly preferred embodiment of the invention, the promoter is the 35 S promoter of CaMV or a promoter of the T-DNA of *Agrobacterium tumefaciens,* for example the promoter of the nopaline synthetase or octopine synthetase gene.

The invention provides in a further embodiment for a transcription termination unit, in particular a 3'-polyadenylation signal, to be located 3'-wards of the nucleotide sequence of the invention, particularly preferably the polyadenylation signal of the NOS gene of *Agrobacterium tumefaciens.*

The present invention provides in another preferred embodiment for the regulatory sequences to be inducible, for example by external factors.

The invention provides in another preferred embodiment for the regulatory sequences of the expression of the nucleotide sequences of the invention controlled thereby to confer tissue specificity and/or timespecificity, for example to bring about expression of an antisense construct specifically in leaves during senescence.

The invention also provides for the nucleotide sequences of the invention, where appropriate in a unit with the regulatory nucleotide sequences assigned to them, to be arranged in the vector together with nucleotide sequences which assist transfer and integration or recombination of the nucleotide sequences of the invention where appropriate with the regulatory nucleotide sequences assigned to them into the genome of a transformed cell. The nucleotide sequences of the invention can therefore be arranged, for example, between the left and right border region, flanked by only one border region in each case and/or interrupted by one or more border regions of *Agrobacterium tumefaciens* or *Agrobacterium rhizogenes.*

The present invention also relates to cells comprising at least one of the aforementioned vectors. In a particularly preferred manner, such cells are bacterial cells, yeast cells or plant cells, in particular plant cells from monocotyledonous or dicotyledonous plants, in particular sugarbeet. The present invention therefore particularly relates to a non-variety-specific cell of a plant which has been transiently or stably transformed with a nucleotide sequence of the invention, in particular which has this nucleotide sequence in its genome, for example in the form of an antisense construct. A plant means a photosynthetically active organism including algae, mosses, ferns and higher plants.

The invention also relates to cell assemblages, tissues, organs, parts of organs, cell cultures, calli, differentiated or undifferentiated cell aggregates, embryos, protoplasts etc. of an organism which have, stably integrated into the genome or transiently present, at least one cell transformed with the nucleotide sequences of the invention. In a particularly preferred manner, the invention relates to leaves, stalks, seeds, roots, storage organs, petals, flower organs etc. of a plant, said organs having at least one cell stably or transiently transformed with the nucleotide sequences of the invention. In a particularly preferred manner, the plants or the parts thereof are transformed in such a way that the transformed nucleotide sequence is stably inherited from generation to generation.

The present invention relates not only to cells, cell assemblages, calli and plant organs but also, of course, to plants, in particular intact fertile plants which have been transformed by means of the nucleotide sequence of the invention and have in at least one of their cells at least one of these sequences, in particular stably integrated in their genome. The transformation preferably takes place, as stated hereinafter, nonbiologically, where agrobacterium-mediated gene transfer is understood to be nonbiological. The resulting cells, and the plant tissues, plant organs, plant parts or plants having these cells, are not variety-specific. On the contrary, the invention is applicable to virtually all plants, plant families or plant genera.

In a particularly preferred manner, the transformed nucleotide sequence is heterologous to the transformed cell, that is to say is not naturally present in the transformed cell, is not present in the artificially generated high copy number, or is not expressed at the place or time at which it is expressed according to the invention. In cases in which the cell to be transformed already has an endogenous identical or similar nucleotide sequence, the cell obtained by the transformation of the invention differs from the initial cell for example in that the introduced nucleotide sequence is present in a different genetic context in the genome, has different regulatory elements, is arranged in antisense orientation to its regulatory elements and/or is present in increased copy number.

The invention accordingly also relates to methods for producing transgenic cells, where the nucleotide sequence of the invention to be transformed is introduced into the cell to be transformed by means of a conventional transformation method, for example microprojectile bombardment, agrobacterium-mediated gene transfer, electroporation, PEG-mediated transformation or the like.

The invention also relates to methods for producing transgenic plants having the nucleotide sequences of the invention, where cells or cell assemblages transformed with the nucleotide sequences of the invention are cultivated and regenerated to intact, preferably fertile, plants. The cultivation and regeneration take place by conventional methods.

The invention also relates to a protein having the activity of a glutamine synthetase, in particular the GS-1 from sugarbeet, the latter being encoded by the nucleotide sequences of the invention, in particular the nucleotide sequence shown in SEQ ID No. 1, particularly preferably an amino acid sequence shown in SEQ ID No. 2. The invention also relates to proteins having the activity of a glutamine synthetase, in particular the GS-1 from sugarbeet, this sequence having modifications such as amino acid exchanges, deletions, additions, inversions or the like, and the protein having the activity of a GS-1 from sugarbeet. The invention also relates to proteins which, at the amino acid level, have a degree of homology (identical amino acids) of at least 90%, preferably 95%, with the sequence shown in SEQ ID No. 2. Proteins of this type can be prepared by employing the nucleotide sequences of the invention as cloning probes or hybridization probes for identifying and cloning homologous genes encoding these proteins.

The invention relates in a further embodiment to monoclonal or polyclonal antibodies against one, of the aforementioned proteins, these antibodies recognizing and binding one or more epitopes of said proteins.

The invention relates in a further embodiment to methods for altering glutamine metabolism in a sugarbeet, in particular for modulating the expression, particularly preferably for repressing, a protein having the activity of a glutamine synthetase, in particular the GS-1 from sugarbeet, where the glutamine synthetase content of the sugarbeet is altered by transforming at least one sugarbeet cell with a vector of the present invention, in particular transforming with a vector having the nucleotide sequence of the invention in antisense orientation, and regenerating a sugarbeet from the transformed cell or an association of cells. A sugarbeet generated in this way is advantageously characterized in that the glutamine synthetase GS-1 normally formed in its leaves during senescence is not formed because the expression of glutamine synthetase GS-1 is prevented because of the antisense construct present at least in the leaves and expressed there, so that the formation of glutamine in the leaves and, eventually, the deposition of the glutamine in the storage root is prevented.

However, the invention also of course relates to methods for altering glutamine metabolism in plants, in particular sugarbeet, according to which the glutamine synthetase content in particular cells or organs is increased, where appropriate at certain times, in particular by transforming gene constructs which make constitutive and/or enhanced expression of the nucleotide sequences of the invention possible.

Further advantageous refinements of the invention are evident from the dependent claims.

The invention is explained in detail by means of examples and drawings belonging thereto.

SEQ ID No. 1 shows the translated region of the cDNA sequence of the GS-1 from sugarbeet.

SEQ ID No. 2 shows the amino acid sequence of the GS-1 from sugarbeet.

SEQ ID No. 3 shows the complete cDNA sequence of the GS-1 from sugarbeet.

Example 1

Cloning of the cDNA for GS-1

Complete RNA was extracted from senescent sugarbeet leaves. This was done by grinding 20 g of leaf material from senescent sugarbeet leaves in liquid nitrogen and transferring into 100 ml of uptake buffer (50 mM Tris-HCl pH 9.0, 100 mM NaCl, 10 mM EDTA, 2% w/v SDS and 0.2 mg/ml proteinase K). This mixture was phenolized twice with phenol/chlorophorm/isoamyl alcohol (25/24/1), precipitated (1/10 volume of 3M NaAc, pH 6.5, one volume of isopropanol, 2 hours at $-20°$ C.) and washed with 70% ethanol. After taking up in 10 ml of $H_2O$, 10 $\mu g$/ml proteinase K and 2×precipitating with ¼ volume of 10 M LiCl at 0° C. for 16 hours, the complete RNA was taken up in 2 ml of $H_2O$ with 10 $\mu g$/ml proteinase K. 5 mg of complete RNA were obtained.

Poly $(A)^+$ mRNA was then isolated on an oligo-dT cellulose column. This was done by incubating 2 ml of complete RNA with 25 ml of binding buffer (400 mM NaCl, 10 mM Tris-HCl, pH 7.5 and 2% SDS) and oligo-dT cellulose (200 mg of oligo-dT cellulose) at room temperature for 30 minutes while shaking gently. The mixture was transferred into a glass column with cotton frit and washed dropwise with a washing buffer (100 mM NaCl, 10 mM Tris-HCL, pH 7.5, 0.2% SDS) until the $OD_{260}$ was constant at 0.005. This was followed by elution with 10 ml of elution buffer (10 mM Tris-HCL, pH 7.5) at 55° C. Precipitation was then carried out with ¹⁄₁₀ volume of 3 M NaAc, pH 6.5 and 2 volumes of ethanol at $-20°$ C. for two hours, and the mixture was taken up in 10 ml of binding buffer. The column purification was then repeated, the eluate was phenolized before the precipitation, and the mRNA pellet was taken up in TE buffer. 50 $\mu g$ of poly $(A)^+$mRNA were obtained.

cDNA-was prepared using a cDNA synthesis kit from Boehringer Mannheim in accordance with a standard protocol (5 $\mu g$ of mRNA employed). The resulting cDNA was ligated into lambda vectors (NM 1149). 4 $\mu g$ of NM 1149 (EcoR I digested) and 0.2 $\mu g$ of CDNA with EcoR I linkers were employed for this. After the ligation, the DNA was packaged in phages (NM 1149). The Gigapack® II gold packaging extract from Stratagene was employed for this in accordance with the standard protocol, using 4 $\mu g$ of DNA and obtaining a titer of 140 000 pfu.

The resulting cDNA bank was screened, as was a cDNA bank from sugarbeet root tissue (Lambda ZAP® II library, Stratagene, cDNA inserted from EcoR I and Not I into the Lambda ZAP® II vector system, titer: 250 000 pfu, vector pBluescript® SK (−) with insertion isolated in accordance with standard protocol by in vivo excision from Lambda ZAP® II) using a heterologous tobacco probe. The heterologous tobacco probe is described in Becker at al (1992) Plant. Molec. Biol. 19, 367–379. For the screening, E. coli bacteria were infected with the lambda phages and plated out. The phage DNA from lyzed bacteria was subsequently transferred to NC membranes (Plaquelift), and the membrane-bound DNA was hybridized with a radiolabeled tobacco GS-1 cDNA probe.

The screening of the cDNA bank with the heterologous tobacco probe was carried out as follows. Firstly a prehybridization was carried out with 6×SSPE, 0.1% SDS, 5×Denhardt's reagent and 500 μg/ml denatured herring sperm at 61° C. for two hours. The hybridization was then carried out at 61° C. for 16 hours with a solution of 3×SSPE, 0.1% SDS, 5×Denhardt's reagent and 500 μg/ml denatured herring sperm. The washing was carried out with 2×SSC and 0.1% SDS at 61° C. for 2×15 minutes. A washing step was then carried out with 1×SSC and 0.1% SDS at 61° C. for 15 minutes.

An autoradiogram of the membrane filters was developed, positive phages were isolated, and the corresponding DNA was extracted. The cDNA found was subcloned into the plasmid pBluescript SK (Stratagene) and sequenced. The nucleotide sequence of the translated region of the cDNA, including the translation start codon ATG, is depicted in SEQ ID No. 1 and has a length of 1068 bp. The complete sequence of the cDNA is depicted in SEQ ID No. 3 and has a length of 1543 bp. The start codon is located in position 199 to 201. The translated region terminates at position 1266. A polyadenylation signal is located in the region of nucleotides 1478 to 1508.

The amino acid sequence derived from SEQ ID No. 1 has a length of 356 amino acids and is depicted in SEQ ID No. 2. The amino acid sequence represents the amino acid sequence of subunit P of the GS-1 from sugarbeet. The protein is about 42 kDa in size and represents the only subunit of the GS-1 isoform which is present in the form of a homooctamer in senescent sugarbeet leaves.

EXAMPLE 2

In vitro Transcription and Translation of the P Subunit

The nucleotide sequence depicted in SEQ ID No. 1 was transcribed and translated in vitro. The cloned GS-1 DNA sequence employed for this was derived from the sugarbeet cDNA from root tissue mentioned in example 1. In order to establish which GS-1 subunit this DNA sequence codes for, an in vitro transcription and translation was carried out with the "Linked in vitro SP 6/T7 Transcription/Translation Kit-radioactive" kit from Boehringer Mannheim. This was done by incubating 0.5 μl (0.5 μg) of plasmid DNA (pBluescript® SK (−) with the GS-1 insert), 5 μl of T7 transcription buffer and 14.5 μl of H$_2$O at 30° C. for 15 minutes. Then 10 μl of transcription reaction solution, 1.6 μl of $^{35}$S-methionine and 38.4 μl of translation mix were incubated at 30° C. for 1 hour.

In addition, a protein extract was prepared from 5 g of sugarbeet leaves of various ages (in order to obtain all the GS-1 subunits for unambiguous identification). This extract was purified by FPLC, and the fractions with the highest GS-1 activities were concentrated. Protein was determined by the method of Bradford and revealed a protein concentration of about 1 μg/μl. Both this extract and the reaction mixture from the in vitro translation (with the radiolabeled GS-1 protein) were mixed with the same volume of urea loading buffer. 20 μl of each of these were together put as sample for an isoelectric focusing (IEF) on an acrylamide capillary gel (1st dimension). Isoelectric focusing took place at 190 V for 16 h.

Together with a protein size standard, the capillary gel was transferred to an SDS gel in order to fractionate the proteins according to their size (2nd dimension). An SDS-PAGE took place at 140 V for 2 h. A Western blot (500 mA; 1 h) was prepared from this gel.

The nitrocellulose membrane was stained with Ponceau Red and the bands of the size standard were marked with a pencil.

After a blocking treatment (1 h), the membrane was incubated (16 h; RT) with the 1st antibody (anti-GS; antibody against barley GS, Roger Wallsgrove, Rothamsted Experimental Station, Harpenden, UK), 1:3 000 in blocking solution). The membrane was then washed 3× with TBS and incubated (3 h; RT) with the second antibody (1:2 000 in blocking solution). After washing three more times, the color reaction with NBT and BCIP was effected by the alkaline phosphatase (10–20 min. 37° C.; dark). The dried membrane with the color-marked spots for the GS-1 subunits was exposed to an X-ray film (exposure: 16 h; RT; dark).

Figure 1:
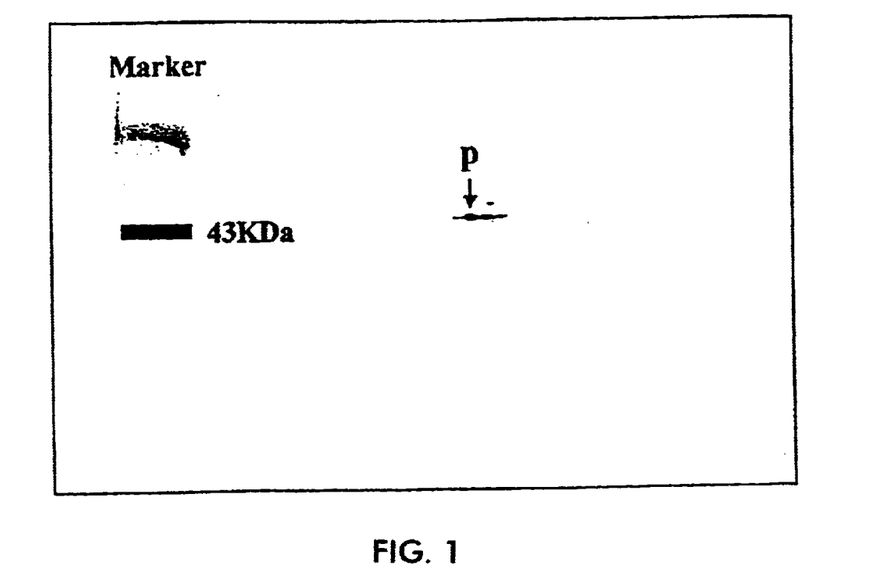
FIG. 1 a Western blot of GS-1 obtained according to the invention.

FIG. 1 shows the membrane filter (Western blot) treated with GS antibodies and colored. The protein size standard is loaded on the left. The pH gradient in this case runs from pH 6 on the left to pH 4 on the right. The 4 spots for the GS-1 subunits are evident at the level of the 43 kDa band (compare FIG. 3, although the sides are reversed in this case). The spot for the P subunit is marked (arrow).

Figure 2:
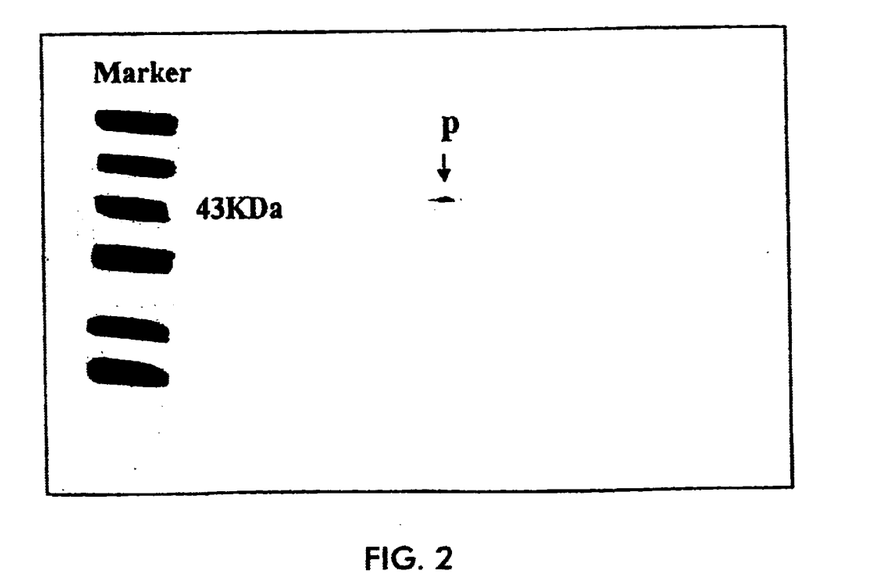
FIG. 2 an autoradiogram of the Western blot in FIG. 1.

FIG. 2 shows the autoradiogram of the membrane on which the bands of the size standard are indicated on the left and a spot appears on the right at the level of the 43 kDa band. This spot was produced by the radiolabeled protein which had been transcribed and translated in vitro. It is possible by comparing the autoradiogram with the membrane to assign a spot on the membrane to the single spot on the film. This spot was identified as subunit "P"(compare FIG. 3).

Figure 3:
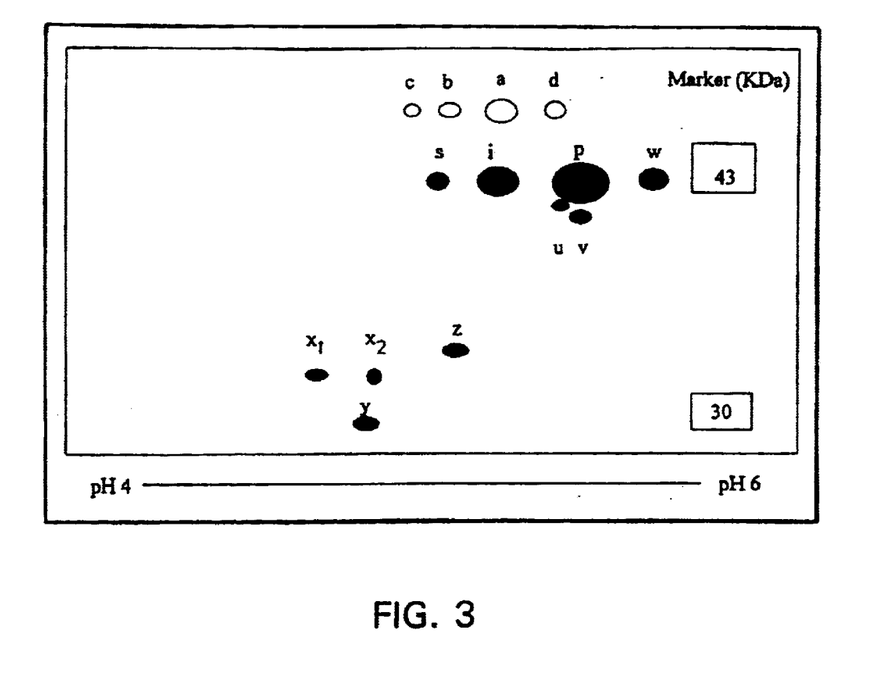
FIG. 3 a diagrammatic depiction of the results obtained in FIGS. 1 and 2.

FIG. 3 represents a diagram of the proteins which can be labeled by GS antibodies. The direction of the pH gradient is indicated at the bottom (1st dimension) from pH 4 on the left to pH 6 on the right. The bands of the size standard (2nd dimension) are depicted on the right from 43 kDa at the top to 30 kDa at the bottom. Spots a, b, c and d, which are white in this diagram, show the positions of the GS-2 subunits, which are likewise recognized by the antibody but can be separated from GS-1 by FPLC. At the level of the 43 kDa band there are four black spots s, i, p and w, which were identifiable on the basis of their size as the subunits forming the octamer of GS-1. The other black spots u, v, $x_1$, $X_2$, y and z are possibly degradation products of the GS proteins.

EXAMPLE 3

Production of Transgenic Sugarbeet

A series of constructs each comprising a promoter which can be expressed in plants, namely the CaMV 35 S promoter, each comprising a section of the sugarbeet GS-1 subunit gene of the invention in antisense orientation, and each comprising the NOS terminator was produced. The sections of the gene of the invention employed differed from one another. The gene cassettes produced in this way were ligated into the binary vector (BIN19 with kanamycin resistance), and *Agrobacterium tumefaciens* (with rifampicin resistance) was transformed with the resulting binary vectors by electroporation. The transformants underwent rifampicin and kanamycin selection. Subsequently, sugarbeet leaf disks and leaf stalks were transformed in a suspension with transformed agrobacteria, and callusing and shooting were induced with the plant hormones NAA and BAP. After selection on kanamycin-containing medium and regeneration to intact plants by conventional protocols, it was possible by means of measurements of the GS1 enzyme activities, SDS gel electrophoreses, 2D PAGE and Northern blot analyses to demonstrate that all the constructs employed, with the various gene sections, were present and active in the leaves of the transgenic, regenerated plant, and led to suppression of glutamine synthetase activity and formation in senescent sugarbeet leaves.

What is claimed is:

1. An isolated nucleotide sequence for reducing or preventing the expression of a protein having the activity of a glutamine synthetase in the senescing leaves of a transgenic plant selected from the group consisting of
   a) the DNA sequence of SEQ ID NOs: 1 and 3,
   b) a nucleotide sequence which encodes the amino acid sequence SEQ ID NO: 2, and
   c) a nucleotide sequence which is complementary to the nucleotide sequences of a) or b),
   where the nucleotide sequence is from sugarbeet.

2. A vector comprising the nucleotide sequence as claimed in claim 1.

3. The vector as claimed in claim 2, where the vector is a plasmid or a viral vector.

4. The vector as claimed in claim 2, where the nucleotide sequence is operatively linked to at least one regulatory nucleotide sequence.

5. The vector as claimed in claim 4, where a promoter controlling the expression of the nucleotide sequence is arranged 5'-wards of the nucleotide sequence.

6. The vector as claimed in claim 4, where a 3'-polyadenylation signal is arranged 3'-wards of the nucleotide sequence.

7. The vector as claimed in claim 4, where the regulatory sequence is inducible.

8. The vector as claimed in claim 4, where the regulatory sequence confers tissue specificity and/or time specificity to the expression of the nucleotide sequence.

9. The vector as claimed in claim 2, where the nucleotide sequence has antisense orientation to the promoter.

10. A bacterial or plant cell comprising the vector as claimed in claim 2.

11. The cell as claimed in claim 10, which is a sugarbeet cell.

12. A plant comprising at least one cell as claimed in claim 10.

13. A seed of a plant, wherein said seed comprises at least one plant cell as claimed in claim 10.

14. A method for altering glutamine metabolism in a sugarbeet, where synthesis of glutamine synthetase senescing leaves in the sugarbeet is prevented or reduced by transforming at least one plant cell with the vector as claimed in claim 3, and regenerating the sugarbeet.

15. A method for producing a transgenic sugarbeet which shows altered glutamine metabolism, where the latter is based on a reduction of the content of glutamine synthetase in senescing leaves and where at least one plant cell is transformed with the vector as claimed in claim 9, and the plant cell is regenerated to an intact plant.

* * * * *